United States Patent
Hanlon et al.

(10) Patent No.: US 10,172,604 B2
(45) Date of Patent: Jan. 8, 2019

(54) TROCAR SYSTEM HAVING A DRIVE

(71) Applicant: Synergetics, Inc., O'Fallon, MO (US)

(72) Inventors: Matthew A. Hanlon, O'Fallon, MO (US); Matthew LaConte, Chesterfield, MO (US)

(73) Assignee: Synergetics, Inc., O'Fallon, MO (US)

( * ) Notice: Subject to any disclaimer, the term of this patent is extended or adjusted under 35 U.S.C. 154(b) by 818 days.

(21) Appl. No.: 14/192,379

(22) Filed: Feb. 27, 2014

(65) Prior Publication Data

US 2014/0180013 A1 Jun. 26, 2014

Related U.S. Application Data

(63) Continuation of application No. 13/656,314, filed on Oct. 19, 2012, now Pat. No. 8,702,742.

(60) Provisional application No. 61/550,012, filed on Oct. 21, 2011.

(51) Int. Cl.
| | |
|---|---|
| *A61B 17/02* | (2006.01) |
| *A61B 17/34* | (2006.01) |
| *A61F 9/007* | (2006.01) |
| *A61B 17/00* | (2006.01) |

(52) U.S. Cl.
CPC ...... *A61B 17/0218* (2013.01); *A61B 17/3415* (2013.01); *A61B 17/3417* (2013.01); *A61B 17/3421* (2013.01); *A61B 17/3468* (2013.01); *A61B 2017/00362* (2013.01); *A61B 2017/3405* (2013.01); *A61F 9/00736* (2013.01)

(58) Field of Classification Search
CPC .... A61B 2017/3447; A61B 2017/3445; A61B 17/3468; A61B 17/068; A61B 17/3421; A61B 17/0218; A61B 17/12163; A61B 2090/3987; A61B 2090/3966; A61B 17/34; A61B 2017/345; A61B 17/3476; A61M 37/0069; A61M 2210/0612; A61F 9/0017; A61F 9/0026; A61F 2230/0069; A61F 2230/0052

See application file for complete search history.

(56) References Cited

U.S. PATENT DOCUMENTS

| | | | | |
|---|---|---|---|---|
| 5,281,197 A | * | 1/1994 | Arias | A61M 37/0069 604/209 |
| 5,320,611 A | * | 6/1994 | Bonutti | A61B 17/0401 604/264 |
| 5,558,637 A | | 9/1996 | Allonen et al. | |
| 5,681,323 A | | 10/1997 | Arick | |
| 5,690,676 A | * | 11/1997 | DiPoto | A61B 17/0401 606/232 |
| 7,331,984 B2 | | 2/2008 | Tu et al. | |

(Continued)

OTHER PUBLICATIONS

International Search Report and Written Opinion of the International Searching Authority regarding PCT/US2012/061130 dated Mar. 6, 2013, 16 pgs.

*Primary Examiner* — Deanna K Hall
(74) *Attorney, Agent, or Firm* — Armstrong Teasdale LLP (57) ABSTRACT

Systems and methods for using a trocar system are disclosed. The system generally includes a handle having a first end a second end, a trocar disposed adjacent the first end of the handle, a plurality of cannulas disposed on the trocar simultaneously, and a drive system. The drive system is disposed for forward movement of the cannulas in a longitudinal direction away from the first end of the handle.

16 Claims, 8 Drawing Sheets

(56) References Cited

U.S. PATENT DOCUMENTS

| | | |
|---|---|---|
| 7,431,710 B2 | 10/2008 | Tu et al. |
| 2004/0050392 A1 | 3/2004 | Tu et al. |
| 2005/0266047 A1 | 12/2005 | Tu et al. |
| 2005/0267478 A1* | 12/2005 | Corradi ................ A61B 17/064 606/916 |
| 2008/0281336 A1* | 11/2008 | Zergiebel ............. A61B 17/068 606/142 |
| 2013/0006286 A1* | 1/2013 | Lavelle .............. A61B 17/3468 606/185 |

* cited by examiner

TROCAR SYSTEM HAVING A DRIVE

CROSS-REFERENCE TO RELATED APPLICATIONS

This patent application is a continuation of U.S. patent application Ser. No. 13/656,314 filed on Oct. 19, 2012, which claims priority to U.S. Provisional Patent Application No. 61/550,012 filed on Oct. 21, 2011, the disclosures of which are hereby incorporated by reference in their entirety.

FIELD

This disclosure generally relates to trocar systems and, more specifically, to trocar systems operable to move a cannula along a trocar.

BACKGROUND

Incisions are formed in a patient's body (e.g., in the eye) in a variety of surgical procedures. Typically, cannulas are inserted into these incisions to keep the incision from closing. Other surgical implements may then be inserted through the cannula into the patient's body after removal of the trocar.

These previous systems are time-consuming, and costly and therefore unsatisfactory. Accordingly, an improved trocar system is needed.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

In one aspect, a trocar system is provided. The trocar system includes a handle having a first end and a second end, a trocar disposed adjacent the second end of the handle, a plurality of cannulas disposed on the trocar, and a drive system. The drive system is disposed for forward movement of the cannulas in a longitudinal direction away from the first end of the handle.

In another aspect, a trocar system is provided. The trocar system includes a handle having a first end and a second end, a trocar disposed adjacent the second end of the handle, at least one cannula disposed on the trocar, and a drive system. The drive system is disposed for forward movement of the at least one cannula in a longitudinal direction away from the first end of the handle. The drive system includes a drive member and a biasing member connected to the drive member to bias the drive member against forward movement in the longitudinal direction.

In yet another aspect, a method of using a trocar system to insert a cannula into an incision formed in a portion of a patient's body is provided. The trocar system includes a handle, a drive member, an actuating member, a trocar, and a plurality of cannulas disposed on the trocar simultaneously. The method includes inserting the trocar into an incision in a portion of the patient's body, inserting a first cannula of the plurality of cannulas into the incision such that the first cannula is disposed between the incision and the trocar, and actuating the actuating member. Actuation of the actuating member engages a tooth on the drive member and moves the drive member forward in a longitudinal direction, and forward movement of the drive member results in forward movement of a second cannula of the plurality of cannulas to a position adjacent an end of the handle.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Like reference symbols in the various drawings indicate like elements.

DETAILED DESCRIPTION

The embodiments described herein generally relate to trocar systems that are operable to move a cannula disposed on one end of a trocar when a user depresses a plunger. Such systems may be used in various surgical procedures such as ophthalmic procedures, and in particular, intra-ocular ophthalmic procedures for vitreo-retinal surgery. Thus, while reference is made herein to use of the system in ophthalmic procedures, it should be understood that the system can also be used in other surgical procedures.

Figure 1:
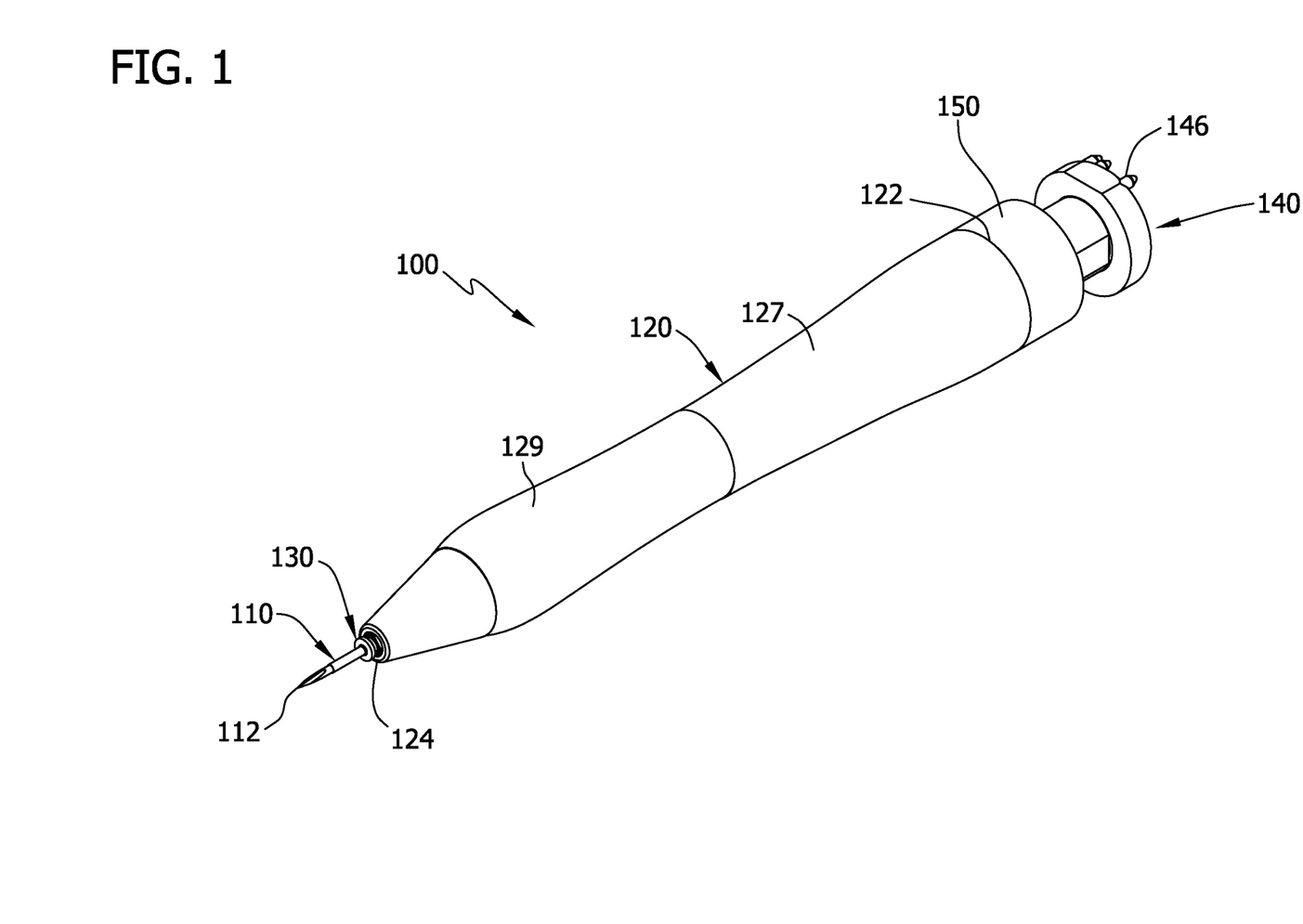
FIG. 1 is a perspective of one embodiment of a trocar system.

An example trocar system is generally indicated by reference numeral 100 in FIG. 1. The system 100 of this embodiment includes a trocar 110, a handle 120, three cannulas 130, and a plunger 140. Other components of the system 100 are discussed in greater detail below.

Figure 8:
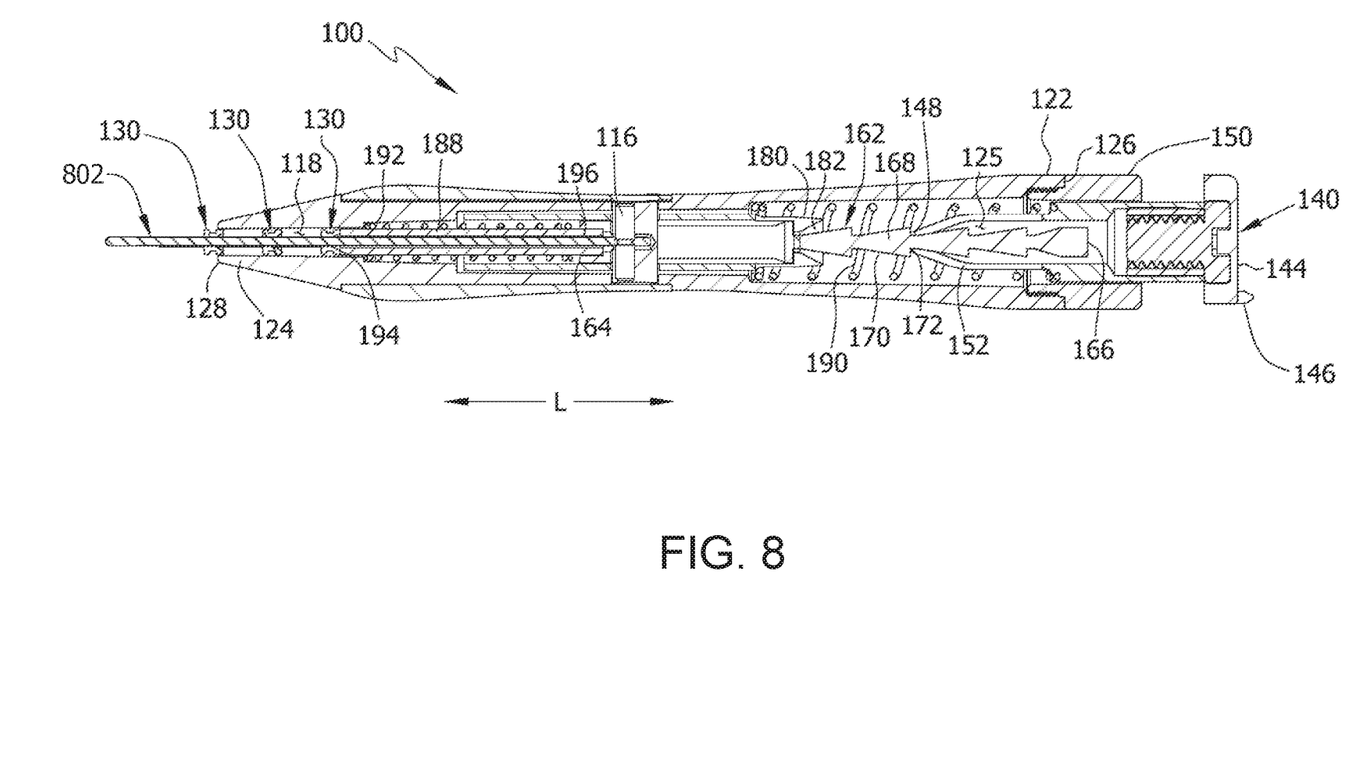
FIG. 8 is a cross-sectional view of the system of FIG. 1 including a blunt insertion device.

Typical trocar 110 configurations include hypodermic needles, lancet-shaped needles, stiletto blades, saber-tipped blades, and beveled rods. Furthermore, in some systems the trocar 110 is a blunt insertion device 802 (FIG. 8) that is used to insert the cannula 130 into an incision formed by another sharp or pointed object.

Figure 3:
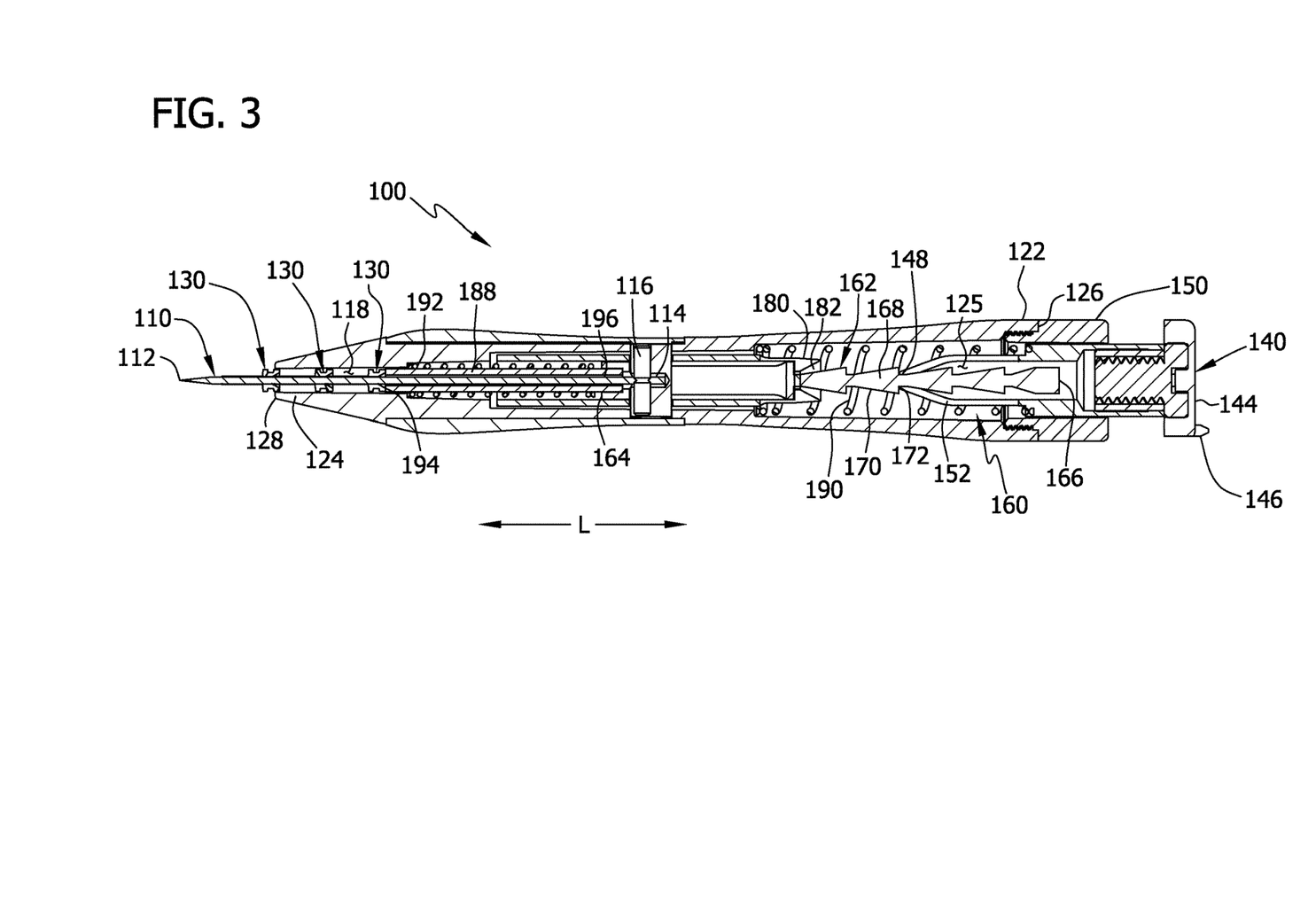
FIG. 3 is cross-sectional view of the system of FIG. 1 taken along line 3-3 of FIG. 2.
Figure 4:
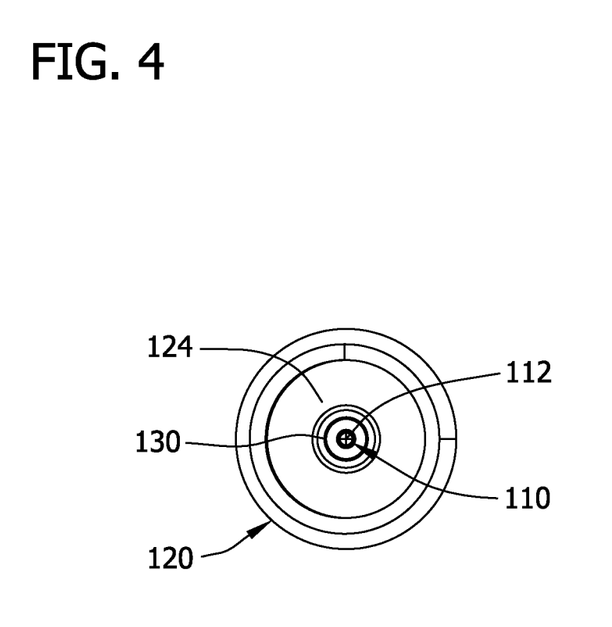
FIG. 4 is an front view of the system of FIG. 1.
Figure 5:
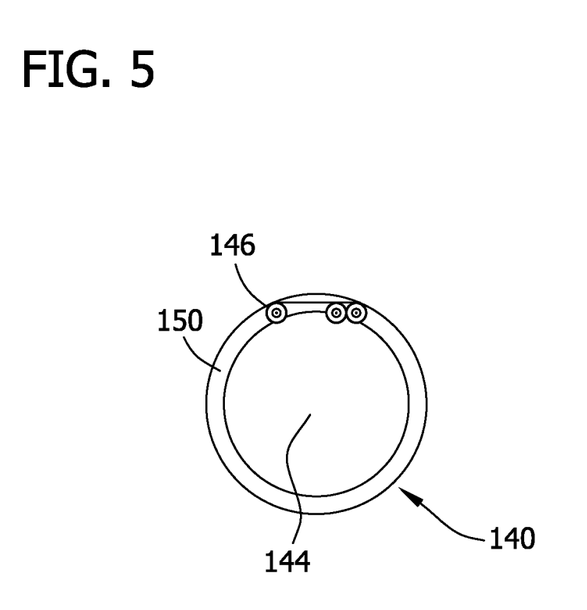
FIG. 5 is a rear view of the system of FIG. 1.
Figure 7:
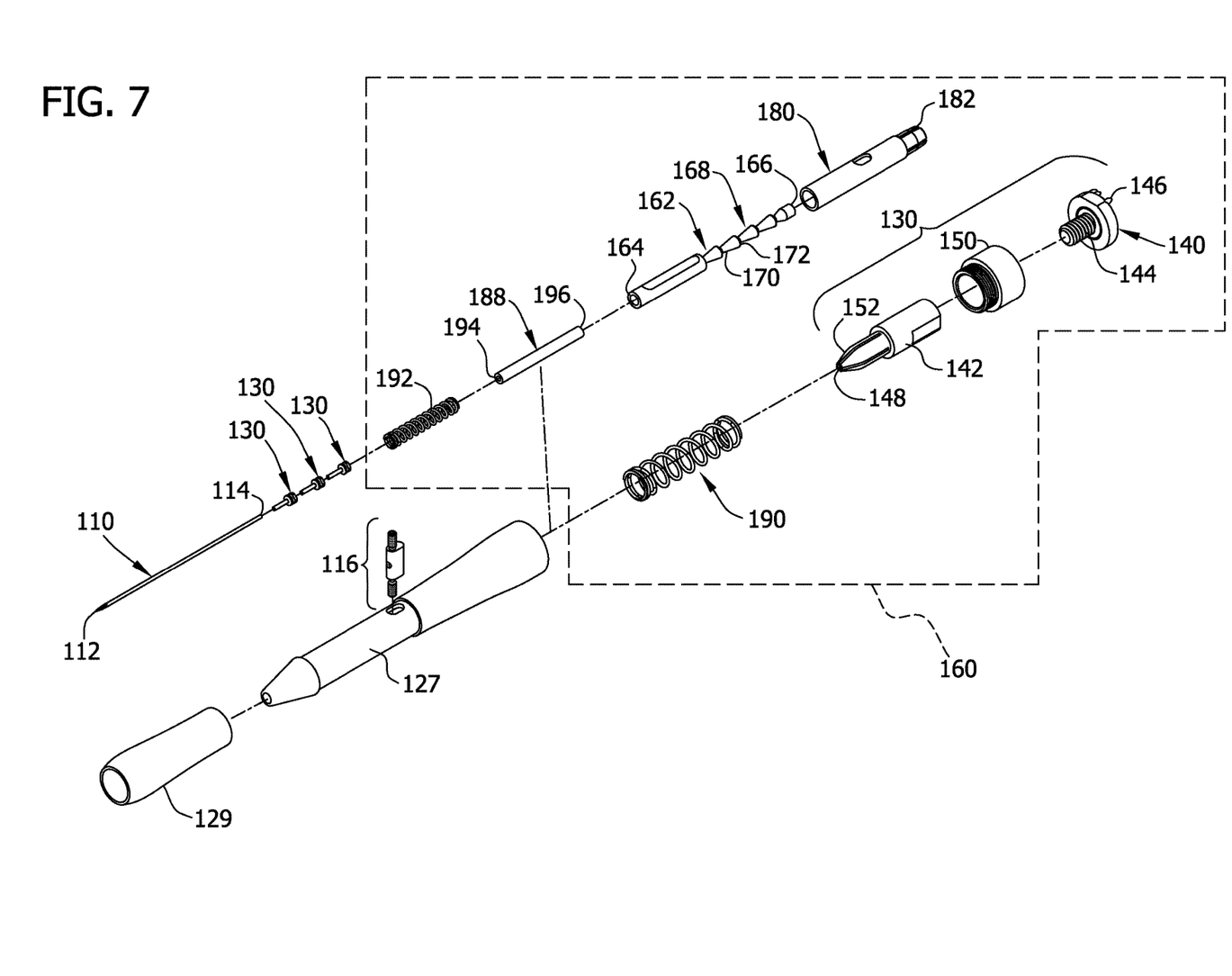
FIG. 7 is an exploded view of the system of FIG. 1.

As best seen in the cross-sectional view of FIG. 3 and exploded view of FIG. 7, the system 100 also includes a drive system 160 comprising a drive member 162, a pawl 180, the plunger 140, a tube 188, a first spring 190, and a second spring 192.

Figure 2:
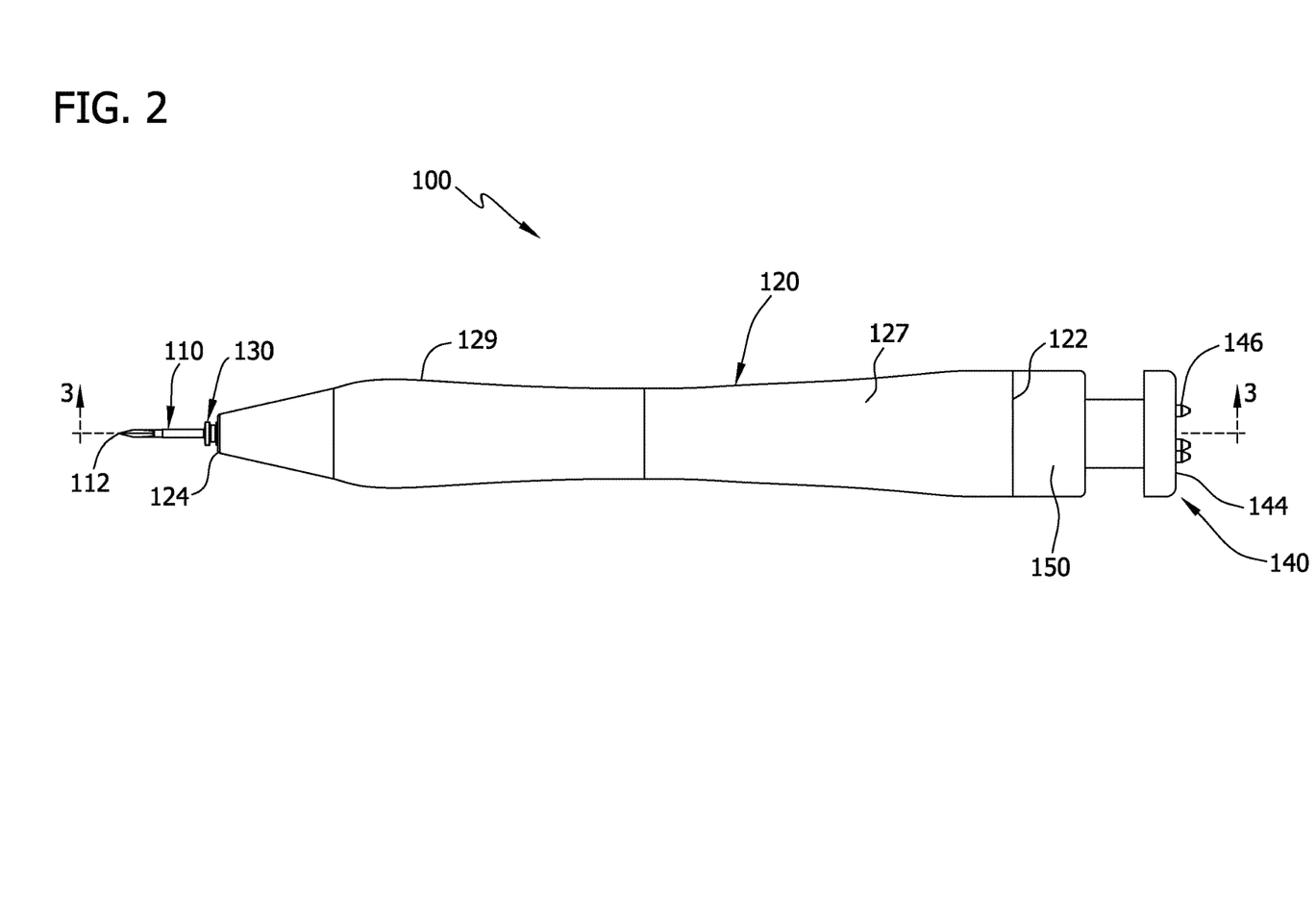
FIG. 2 is a side view of the system of FIG. 1.

As shown in FIGS. 1-3, the trocar 110 has a first end 112 having a sharp point for piercing a portion of a patient's body (e.g., a patient's eye) and forming an incision therein. An opposing second end 114, seen best in FIG. 3, is disposed away from the first end 112 of the trocar 110 and is received within the handle 120. The second end 114 is connected to the handle 120 by a wire lock 116, although other embodiments may use different types of fastening systems (e.g., other mechanical fasteners and/or adhesives).

As shown in FIG. 1, the handle 120 has a first end 122 and an opposing second end 124 opposite from the first end. A first opening 126 is formed adjacent the first end 122 and a second opening 128 is likewise formed adjacent the second end 124. The handle also has a hollow interior section 125 (FIG. 3) and an outer surface 127, a portion of which receives an ergonomic rubberized grip 129 (FIGS. 1 and 3). The grip 129 aids a user grasping the handle 120 and provides a comfortable gripping surface.

Figure 6:
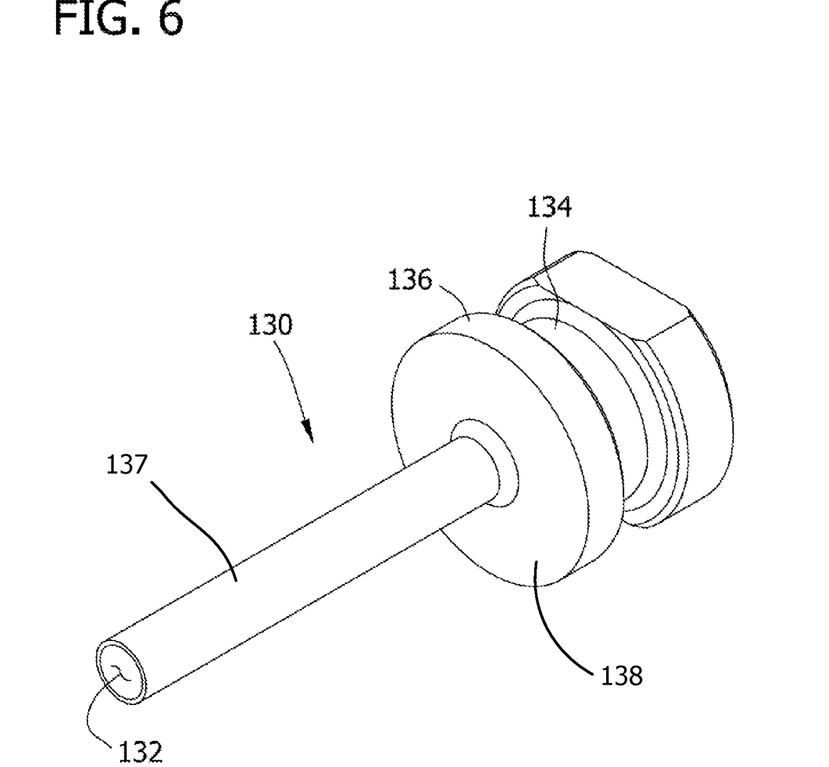
FIG. 6 is an enlarged view of one of the cannulas of the system of FIG. 1.

Cannulas 130, one of which is shown in greater detail in FIG. 6, have a central opening 132 sized to receive the trocar 110. That is, the central opening 132 has a diameter slightly larger than a diameter of the trocar 110. As shown in FIG. 6, the central opening 132 is defined by a cylindrical tube 137 extending from an annular flange 138. The tube 137 has a smooth, cylindrical outer surface. In use, the cannula 130 is positioned within the incision formed by the first end 112 of the trocar 110. The cannula 130 keeps the incision from collapsing or closing after removal of the trocar 110 so that other surgical implements can be inserted through the central opening 132 and into the patient's body.

In the example embodiment, three cannulas 130 are positioned on the trocar 110, although in other embodiments different numbers of cannulas may be used. Moreover, in the example embodiment all of the cannulas 130 except one are positioned on the trocar such that they are disposed in a recess 118 in the second end 124 of the handle 120. Only the most proximal cannula protrudes from the second end 124 of the handle 120. Retention members (e.g., crush ribs) can be positioned in the recess 118 to prevent unintentional movement of the cannulas 130 from the recess.

The plunger 140, broadly an actuating member, is positioned adjacent the first end 122 of the handle 120 and a portion 142 of the plunger is received within the hollow interior section of the handle. As shown in FIG. 3, the plunger 140 travels through the first opening 126 of the handle 120 and keyway 150. The plunger 140 has a first end 144 with a sclera marker 146 and a second end 148 that is generally configured to move the drive member 162 forward in a longitudinal direction L towards the second end 124 of the handle. In this embodiment, the sclera marker 146 is made integral with the plunger, but the marker may have other configurations in other embodiments The plunger 140 has a keyway 150 (FIG. 3) disposed adjacent its first end 144 that couples to the first end 122 of the handle 120 to limit the distance which plunger can be depressed (referred to as a depression distance). Portion 142 is fitted to keyway 150 to prevent rotational movement within handle 120. In some embodiments, the plunger 140 is not used and instead the drive member 162 is extended such that it protrudes from the first end 122 of the handle 120. The user thereby actuates the drive member 120 directly, rather than indirectly with the plunger 140.

In still other embodiments, the actuating member can be disposed for depression by a user in a direction other than the longitudinal direction L to move the drive member 162 forward. For example, the actuating member may be disposed for depression in a direction radial to the longitudinal direction L to move the drive member 162 forward in the longitudinal direction. The actuating member and/or drive member 162 may also rotate when moved in the longitudinal direction L. For example, the actuating member and/or drive member 162 may be components in a screw and/or worm drive.

The drive member 162 (FIG. 3) is elongate and has a first end 164 disposed opposite from a second end 166. The drive member 162 is positioned within the hollow interior section 125 of the handle 120 and has a plurality of teeth 168 disposed on its surface, each of which have a sloped portion 170 and a backside 172. In the example embodiment, there are five teeth 168 while other embodiments may use a drive member having more or less teeth. The second end 148 of the plunger 140 is disposed to selectively engage teeth 168 to move the drive member 162 forward in the longitudinal direction L. This forward movement is towards the first end 112 of the trocar 110.

The pawl 180 (FIG. 3), broadly a detent mechanism, is positioned within the hollow interior section 125 and is disposed to selectively engage teeth 168 to prevent rearward movement of the drive member 162 in the longitudinal direction L. The pawl 180 also has a sloped portion 182 that is complementary to the sloped portions 170 of the teeth 168. The pawl 180 deflects away from the drive member 162 upon contact of its sloped portion 182 with one of the sloped portions 170 of the teeth 168. This deflection permits the teeth 168 to move through the pawl 180 as the plunger 140 moves the drive member 162 forward in the longitudinal direction L.

The pawl 180 includes a resilient material so that it returns to its undeflected position after the tooth 168 has moved far enough forward in the longitudinal direction L where its sloped portion 170 is not in contact with the sloped portion 182 of the pawl 180. The pawl 180 then engages the backside 172 of the tooth 168 upon any attempted rearward movement of the drive member 162. The pawl 180 and the backside 172 of the tooth 168 are in locking engagement as a result of this attempted rearward movement such that the pawl cannot be deflected by the backside of the tooth. Accordingly, the pawl 180 prevents rearward movement of the drive member 162.

In other embodiments, the detent mechanism is a member biased in a direction radial to the longitudinal direction L. The member is disposed for selectively engaging indentations or other indexing features on the drive member 162 to selectively limit rearward movement of the drive member.

A portion 152 of the plunger 140 is disposed to deflect away from the teeth 168 upon contact with their sloped portions 170. The portion 152 includes a resilient material such that it returns to its undeflected position after the teeth 168 pass through. This deflection permits rearward movement of the plunger 140 with respect to the drive member 162. The second end 148 of the plunger 140 engages the backside 172 of one of the teeth 168 when depressed by a user. This engagement results in forward movement of the drive member 162 in the longitudinal direction L.

A first spring 190 is positioned within the hollow interior section 125 of the handle 120. It is connected to the plunger 140 and a portion of the handle 120 and biases the plunger against forward movement in the longitudinal direction L. This spring 190 is a compression spring in the example embodiment, although in other embodiments the spring may be any suitable type of spring or biasing device.

A second spring 192 is also positioned within the hollow interior section 125 of the handle 120. It is connected to the drive member 162 and a portion of the handle and biases the drive member against forward movement in the longitudinal direction L. This spring 192 is a compression spring in the example embodiment, although in other embodiments the spring may be any suitable type of spring or biasing device.

As shown in FIG. 3, a tube 188 connects the drive member 162 to the most rearward cannula (i.e., the cannula positioned nearest the drive member). Forward movement of the drive member 162 results in forward movement of the cannula 130 connected to the tube 188. A first end 194 of the tube 188 is connected to the most rearward cannula 130. A second end 196 of the tube 188 is connected to the drive member 162. In the example embodiment, the second end 196 of the tube 188 is received within a recess formed in the drive member 162 adjacent the first end 164 of the drive member 162.

Forward movement of the most rearward cannula 130 results in forward movement of the other cannulas positioned adjacent to it on the trocar 110. In other embodiments, a tube is not used and instead the most rearward cannula 130 is directly connected to the drive member 162 without any intervening member (e.g., the tube). Alternatively, another structure or connection device may be used to connect the drive member 162 to the cannulas 130.

Cannulas 130 are first positioned on the trocar 110 prior to usage of the system 100. In the example embodiment, three cannulas 130 are used while in other embodiments more or less cannulas can be used.

In use, generally, the user depresses the plunger 140 to move the cannulas 130 forward in the longitudinal direction L along the trocar 110. Depression of the plunger 140 until the keyway 150 prevents further travel results in the movement of the cannulas 130 such that another cannula protrudes from the handle 120.

In the example embodiment, the first end 112 of the trocar 110 is used to pierce a portion of a patient's body (e.g., the patient's eye) and cut an incision therein. In other embodiments, the piercing action can be performed by a separate sharp or pointed object and the trocar 110 is a blunt insertion device onto which the cannulas 130 are installed.

The trocar 110 is then inserted into the patient's body through this incision. As described in greater detail below, the drive system 160 is then used to move the cannulas 130 forward in the longitudinal direction L. In other embodiments, the drive system 160 is used to move the cannulas 130 forward prior to insertion of the trocar 110 into the incision or usage of the trocar to form the incision.

The second end 148 of the plunger 140 is then depressed by the user resulting in engagement of the drive member 162 by the first end 144 of the plunger. The first end 144 of the plunger 140 engages the backside 172 of one of the teeth 168 and thus forward motion of the plunger results in likewise forward movement of the drive member 162. As the drive member 162 moves forward in the longitudinal direction L, the sloped portion 170 of one of the teeth 168 deflects the sloped portion 182 of the pawl 180. This deflection permits the tooth 168 to move through the pawl 180.

The forward movement of the drive member 162 in turn results in forward movement of the cannulas 130 disposed on the trocar 110. As described above, the tube 188 connects the most rearward cannula 130 to the drive member 162 in the example embodiment. The depression of the plunger 140 until the keyway 150 prevents further travel of the plunger results in moving the cannulas 130 a distance such that another cannula protrudes from the second end 124 of the handle 120. The representation of FIG. 3 depicts the system 100 after it the plunger 140 has been depressed to move the cannulas 130 forward such that one cannula protrudes from the second opening 128 in the second end 124 of the handle 120.

The user then releases the plunger 140 and the first spring 190 returns the plunger to its initial, undepressed position (as shown in FIG. 3). As the plunger 140 returns to its initial position, the portion 152 of the plunger against its second end 148 is deflected by contact with the sloped portion 170 of the tooth 168. This deflection permits rearward movement of the plunger 140.

The pawl 180 prevents rearward movement of the drive member by engaging the backside 172 of the tooth 168. After the sloped portion 170 of the tooth 168 travels through the pawl 180, the pawl returns to its undeflected position. The pawl 180 and the backside 172 of the tooth 168 are in locking engagement such that when engaged the pawl cannot be deflected by the backside of the tooth. In this undeflected position, the pawl 180 prevents rearward movement of the drive member 162. The second spring 192 biases the drive member 162 against forward movement to prevent unintended forward movement. The second spring 192 also ensures that the backside 172 of the tooth 168 remains in contact with the pawl 180 until depression of the plunger 140. After release of the plunger 140 and the rearward movement of the plunger, the system is set to move forward another cannula 130 forward from the second opening 128 in the second end 124 of the handle 120.

The most proximal cannula 130 (i.e., the protruding cannula) is then grasped by a user (e.g., a surgeon, and typically with the aid of a tool such as forceps) and moved from its position adjacent the second end 114 of the trocar 110 towards the first end 112. In the example embodiment, the cannula has a circumferential groove 134 formed in its outer surface 136 (FIG. 3) to aid in the grasping of the cannula by the tool.

Once positioned near the first end 112 of the trocar 110, the cannula 130 is slid into the incision such that it is positioned between the incision and the trocar. The trocar 110 is then removed from the central opening 132 of the cannula 130 by sliding the trocar in a direction away from the patient's body. Another surgical implement may then be inserted into the central opening 132 of the cannula 130 and used in the surgical procedure. Examples of such surgical implements include fiber optic lights, lasers, probes, infusion systems, or other surgical tools. After completion of the surgical procedure the cannula 130 is removed from the incision.

The method can then be repeated to use the system to pierce another portion of the patient's body and insert a cannula in the incision. Thus, when the method is repeated the plunger is depressed again to move another cannula forward such that it protrudes from the recess in the first end of the cannula. This cannula is then placed in the incision and the trocar is withdrawn from the cannula and another surgical implement is inserted into the central opening of the cannula. The method can again be repeated until all of the cannulas have been inserted into incisions in the patient's body.

In some embodiments, the system 100 may be cleaned/reconditioned and reused after the cannulas 130 have been removed from the system. In such embodiments, a tool is used to disengage the drive member from the pawl 180 such that drive member 162 can be moved to its rearward-most position. This tool engages the sloped portion 182 of the pawl 180 and deflects outward to such a degree that the teeth 168 of the drive member 162 are able to pass through the pawl without interference. Additional cannulas 130 can be placed on the trocar 110 and the system 100 can be reused after appropriate cleaning procedures are performed on the system.

The systems and methods described herein position multiple cannulas on a single trocar. The trocar can be used to cut multiple incisions in the patient's body and insert one of the cannulas into each incision. Thus, the system can be used to cut each of the separate incisions necessary in a typical surgical procedure and place cannulas therein without the need to place a cannula on the trocar prior to placement of the cannula in the incisions. This reduces both the amount of time required to cut the incisions and place the cannulas therein. The cost of the procedure is reduced as well since only one tool is used to cut multiple incisions and place cannulas in the incisions.

When introducing elements of the present invention or the embodiments thereof, the articles "a", "an", "the" and "said" are intended to mean that there are one or more of the elements. The terms "comprising", "including" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above constructions and methods without departing from the scope of the invention, it is intended that all matter contained in the above description and shown in the accompanying figures shall be interpreted as illustrative and not in a limiting sense.

What is claimed is:

1. A trocar system comprising:
   a handle having a first end and a second end;
   a trocar disposed adjacent the second end of the handle;
   a plurality of cannulas disposed on the trocar simultaneously, wherein each cannula includes an annular flange and a cylindrical tube that extends from the flange and defines a central opening sized to receive the trocar therein, the central opening defined at a distal tip of the cannula, wherein the tube has a smooth, cylindrical outer surface that extends to the distal tip of the cannula; and
   a drive system operatively connected to at least one of the cannulas and disposed for forward movement of the cannulas in a longitudinal direction away from the first end of the handle.

2. The trocar system of claim 1 wherein the drive system is configured for incremental movement of the cannulas in the forward direction.

3. The trocar system of claim 1 wherein the drive system comprises:
   a drive member positioned within a hollow interior section of the handle having a first end a second end and disposed for moving the cannulas in the longitudinal direction away from the first end of the handle; and
   a detent mechanism positioned within the hollow interior section and disposed to selectively engage the drive member to limit rearward movement of the drive member in the longitudinal direction towards the first end of the handle.

4. The system of claim 3 further comprising an actuating member connected to the drive member and disposed to move the drive member in the forward direction.

5. The system of claim 4 wherein the actuating member comprises a plunger disposed for depression by a user in the forward direction to move the drive member in the forward direction.

6. The system of claim 3 wherein the detent mechanism is a member biased in a direction radial to the longitudinal direction and disposed for selectively engaging indentations in the drive member to limit rearward movement of the drive member.

7. The trocar system of claim 1 wherein the trocar comprises a blunt insertion device.

8. The trocar system of claim 1 wherein the trocar is shaped for piercing a portion of a patient's body and making an incision therein.

9. The trocar system of claim 3 wherein the drive system further comprises a connection device interconnecting the drive member to at least one of the plurality of cannulas, the connection device configured to move forward in the longitudinal direction while the trocar remains stationary.

10. The trocar system of claim 9 wherein the connection device comprises a tube disposed on the trocar.

11. The trocar system of claim 1, wherein the drive system further includes a plunger that extends axially from the first end of the handle and is depressible by a user in the forward direction to actuate the drive system and move the cannulas in the forward direction.

12. A method of using a trocar system to insert a cannula into an incision formed in a portion of a patient's body, the trocar system comprising a handle having a first end and a second end, a drive system including a drive member and an actuating member, a trocar disposed adjacent the second end of the handle, and a plurality of cannulas disposed on the trocar simultaneously, each cannula including an annular flange and a cylindrical tube that extends from the flange and defines a central opening sized to receive the trocar therein, the central opening defined at a distal tip of the cannula, the tube having a smooth, cylindrical outer surface that extends to the distal tip of the cannula, the method comprising:
   inserting the trocar into an incision in a portion of the patient's body;
   inserting a first cannula of the plurality of cannulas into the incision such that the first cannula is disposed between the incision and the trocar; and
   actuating the actuating member, wherein actuation of the actuating member engages a tooth on the drive member and moves the drive member forward in a longitudinal direction, wherein forward movement of the drive member results in forward movement of a second cannula of the plurality of cannulas in the longitudinal direction away from the first end of the handle to a position adjacent the second end of the handle.

13. The method of claim 12 further comprising removing the trocar from the first cannula.

14. The method of claim 13 further comprising:
   inserting the trocar into a second portion of the patient's body, wherein insertion of the trocar forms a second incision in the second portion of the patient's body; and
   inserting the second cannula into the second incision such that the second cannula is disposed between the second incision and the trocar.

15. The method of claim 12 wherein inserting the trocar into the patient's body cuts the incision in the portion of the patient's body.

16. The method of claim 12 wherein the actuating member includes a plunger, and actuating the actuating member comprises depressing the plunger.

* * * * *